United States Patent
Perrin et al.

(10) Patent No.: US 12,329,877 B2
(45) Date of Patent: Jun. 17, 2025

(54) SURGICAL GLUES BASED ON MONOMERS COMPRISING A PHOSPHATE FUNCTION

(71) Applicants: COHESIVES, Dijon (FR); CENTRE NATIONAL DE LA RECHERCHE SCIENTIFIQUE, Paris (FR); UNIVERSITE DE HAUTE ALSACE, Mulhouse (FR)

(72) Inventors: Bertrand Perrin, Dijon (FR); Ariane Aubin, Mulhouse (FR); Jacques Lalevee, Mulhouse (FR); Jean-Philippe Schwebelen, Burnhaupt-le-Haut (FR)

( * ) Notice: Subject to any disclaimer, the term of this patent is extended or adjusted under 35 U.S.C. 154(b) by 759 days.

(21) Appl. No.: 17/431,285

(22) PCT Filed: Feb. 19, 2020

(86) PCT No.: PCT/EP2020/054387
§ 371 (c)(1),
(2) Date: Aug. 16, 2021

(87) PCT Pub. No.: WO2020/169681
PCT Pub. Date: Aug. 27, 2020

(65) Prior Publication Data
US 2022/0125988 A1    Apr. 28, 2022

(30) Foreign Application Priority Data
Feb. 21, 2019 (FR) .................................. 1901771

(51) Int. Cl.
*A61L 24/04* (2006.01)
*C08F 22/20* (2006.01)

(52) U.S. Cl.
CPC ............ *A61L 24/043* (2013.01); *C08F 22/20* (2013.01); *A61L 2300/802* (2013.01); *A61L 2400/04* (2013.01); *C08F 2810/20* (2013.01)

(58) Field of Classification Search
CPC ............. A61L 24/043; A61L 2300/802; A61L 2400/04; C08F 22/20; C08F 2810/20
See application file for complete search history.

(56) References Cited

U.S. PATENT DOCUMENTS 4,918,136 A * 4/1990 Kawaguchi ................ C09J 4/00
526/318.41
2017/0209617 A1    7/2017 Skaria et al.

FOREIGN PATENT DOCUMENTS

| WO | 2008082929 A2 | 7/2008 | |
|---|---|---|---|
| WO | 2016011028 A1 | 1/2016 | |
| WO | WO-2016185153 A1 * | 11/2016 | ....... A61B 17/00491 |

OTHER PUBLICATIONS

International Search Report and Written Opinion issued on Apr. 23, 2020 in corresponding International Application No. PCT/EP2020/054387; 12 pages.
International Preliminary Report on Patentability issued on Jun. 11, 2021 in corresponding International Application No. PCT/EP2020/054387; 19 pages.

* cited by examiner

*Primary Examiner* — Lezah Roberts
*Assistant Examiner* — Abdulrahman Abbas
(74) *Attorney, Agent, or Firm* — Maier & Maier, PLLC

(57) ABSTRACT

A composition for use as a surgical adhesive for the adhesion of a material to a biological tissue, for the adhesion of biological tissues to one another, for the adhesion of a glue or of a substance to the surface of a biological tissue, as a surgical sealant, for blocking or plugging orifices created by a thread suture or staple suture or by a tissue resection, for blocking an orifice, an incision or a tear in a biological tissue, as a hemostatic agent for stopping bleeding, as a dressing on a biological tissue for covering and protecting a wound, for reinforcing a biological tissue, for attaching and stabilizing a biological tissue. The compositions include a polymerizable monomer with a phosphate function or a phosphonate function and a methacrylate function.

14 Claims, No Drawings

SURGICAL GLUES BASED ON MONOMERS COMPRISING A PHOSPHATE FUNCTION

TECHNICAL FIELD

The present invention relates in particular to compositions to be used as a surgical adhesive, a surgical sealing product, haemostatic dressing and cutaneous dressing. More particularly, the present invention relates to compositions intended to be used in a method:
- as a surgical adhesive for the adhesion of a material to a biological tissue,
- for the adhesion of biological tissues to one another,
- for the adhesion of a glue or a substance to the surface of a biological tissue,
- as a surgical sealant,
- for blocking or plugging orifices created by a thread suture or staple or by a tissue resection (haemostasis, aerostasis, lymphostasis for example),
- for blocking an orifice, an incision or a tear in a biological tissue,
- as a haemostatic agent for stopping bleeding, alone or in addition to conventional haemostasis techniques such as suturing, compression or electrocoagulation,
- as a dressing on a biological tissue for covering and protecting a wound, These compositions may also be used:
- for reinforcing biological tissue,
- for fixing and stabilising biological tissue.

PRIOR ART

A number of surgical techniques involve the use of surgical glues. The latter are mainly used to help achieve surgical haemostasis. However, the efficacy of surgical glues in this indication is controversial and other uses such as aerostasis do not show better results.

Furthermore, surgical glues have very poor adhesive properties and therefore cannot be used as an adhesive or as a surgical suture. The application of surgical glues is mostly done directly onto the tissue, without preparation of the bonding surface. The penetration into the tissues is poor or non-existent which results in a poor quality bonding. The applicants have confirmed that current glues do not stick and do not penetrate into the tissues.

In order to address this problem, low viscosity surgical glues have been proposed. These surgical glues penetrate more easily into the tissue and thus provide a better bond.

However, these surgical glues require high concentrations of monomers. Furthermore, their chemical nature can cause burns at the application site.

As a consequence, the present invention proposes providing a new type of surgical glues. The compositions and the method according to the invention make it possible to obtain effective and strong bonding with lower quantities of monomers than the glues of the prior art. In addition, contrary to the glues of the prior art, the surgical glues according to the invention do not cause burns to the skin.

SUMMARY OF THE INVENTION

The present invention relates in particular to compositions for use as a surgical adhesive, a surgical sealing product, haemostatic dressing and cutaneous dressing. More particularly, the present invention relates to compositions for use as surgical adhesive for the adhesion of a material to a biological tissue, for the adhesion of biological tissues to one another, for the adhesion of a glue or a substance to the surface of a biological tissue, as surgical sealant, for blocking or plugging orifices created by a thread suture or staple or by a tissue resection, for blocking an orifice, an incision or a tear in a biological tissue, as a haemostatic for stopping bleeding, as a dressing on a biological tissue for covering and protecting a wound, for reinforcing a biological tissue, for fixing and stabilising a biological tissue, notable in that said compositions comprise a polymerisable monomer comprising a phosphate function or a phosphonate function and a methacrylate function.

According to a preferred embodiment of the invention said polymerisable monomer comprises a phosphate function and a methacrylate function.

The applicants have been able to demonstrate that the presence of a phosphate function or phosphonate in said monomer makes it possible to obtain a composition that has adhesive capacities and is safer than compositions comprising a chemically equivalent monomer comprising a methacrylate function but no phosphate function.

Preferably, the polymerisable monomer is of formula I, wherein [Chem 1]

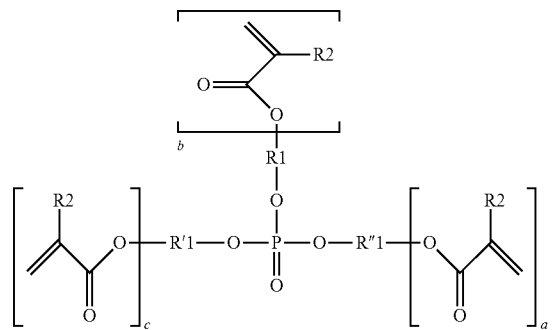

R2 is H or CH3;
R1, R1', R1" are independently of one another a linear polyether radical, a linear or branched aliphatic radical of C1-C50, an aromatic radical of C6-C18, for which the carbon chain of said radicals can be interrupted by O, S, OCONH and/or can comprise one or more alcohol functions;
R1" is H if a=0;
b is 1;
a or c is 1 or 0.

The term "the carbon chain of said functions may be interrupted" means that said functions are inserted into the carbon chain, i.e. are linked to carbon atoms on both sides.

Preferably, a=0, R2=H or CH$_3$ and R'1 and R1 is a linear aliphatic chain of C1-C12.

Even more preferably, a=0, c=0, R2=CH$_3$ and R1 is a linear aliphatic chain of C1-C12.

Preferably, a=0, c=0, R"1=H, R'1=H, R1=linear aliphatic chain of C1-C12, b=1, R2=CH$_3$.

Preferably, a=1, c=1, b=0, R1=H, R'1=R"1=linear aliphatic chain of C1-C12, R2=CH$_3$.

Preferably, the polymerisable monomer of formula I is 10-MDP ($C_{14}H_{27}O_6P$) or MEP($C_{12}H_{19}O_8P$).

According to another preferred embodiment, the polymerisable monomer of formula I is selected from glycerol dimethacrylate phosphate, ethylene glycol methacrylate phosphate, polyethylene glycol methacrylate phosphate, methacryloyloxydecyl hydrogen phosphate, methacryloyloxy ethyloxy hydrogen phosphate, glycerol monomethacrylate phosphate, triethylene glycol monomethacrylate phosphate, methacryloyloxy propyl phosphate, methacryloyloxy hexyl phosphate, methacrylate amino ethyl phosphoric acid, bis(glyceryl dimethacrylate) phosphate and mixtures thereof.

In the context of the present invention the term "polymerisable monomer" means designating a monomer whose polymerisation can be initiated by a physical or chemical activator.

According to a preferred embodiment, the polymerisation is initiated by the effect of UV radiation. In a preferred manner, said UV radiation has a wavelength between 200 nm to 400 nm, even more preferably between 300 nm to 400 nm and most preferably between 350 nm and 400 nm.

According to another preferred embodiment, the polymerisation is initiated by the effect of radiation of wavelength between 400 nm and 500 nm.

According to a preferred embodiment, the polymerisation is initiated by a chemical activator.

The polymer obtained after polymerisation of the monomer is preferably a biocompatible polymer.

Preferably, the viscosity of the composition according to the invention is less than 200 mPa·s at 20° C.

The viscosity of the composition may in particular be measured by a falling-ball viscometer according to standard DIN53015.

According to a preferred embodiment, said viscosity is less than 120 mPa·s at 20° C.

According to an even more preferred embodiment, said viscosity is less than 50 mPa·s at 20° C.

According to a much preferred embodiment, said viscosity is less than 20 mPa·s at 20° C.

According to a preferred embodiment, the composition according to the invention is not a hydrogel.

According to a preferred embodiment, said monomer has a molar mass between 250 and 500 g·mol−1.

According to a preferred embodiment, said monomer has a concentration between 10 and 60% by mass in relation to the total mass of the composition.

According to an even more preferred embodiment, said monomer has a concentration between 40 and 90% by mass in relation to the total mass of the composition.

According to a preferred embodiment, said composition further comprises between 4% and 30%, by mass in relation to the total mass of the composition, of a first cross-linking agent.

The person skilled in the art is capable of selecting the most suitable cross-linking agent as a function of the polymerisable monomer used.

According to a preferred embodiment, said first cross-linking agent comprises an acrylate function or a methacrylate function.

According to a preferred embodiment, said first cross-linking agent is selected from the group comprising multifunctional acrylates and methacrylates comprising in particular 1,6-hexanediol diacrylate, trimethylolpropane triacrylate, 1,2-ethylene glycol dimethacrylate, pentaerythritol tetracrylate, I 3-(acryloyloxy)-2-hydroxypropyl methacrylate (AHM), urethane dimethacrylate (UDMA), hexanediol dimethacrylate (HDDMA), triethyleneglycol dimethacrylate (TEGDMA), and mixtures thereof.

According to another preferred embodiment, said first cross-linking agent is selected from the group comprising multifunctional acrylates comprising in particular hexanediol dimethylacrylate (HDDMA), ethylene glycol dimethacrylate (EGDMA), butanediol diacrylate (BDDA), poly(ethylene glycol) diacrylate (PEGDA) and mixtures thereof.

According to a preferred embodiment, said first cross-linking agent is UDMA and has a concentration between 4.5% and 5% by mass in relation to the total mass of the composition.

According to a preferred embodiment, said first cross-linking agent is TEGDMA and has a concentration between 25% and 30% by mass in relation to the total mass of the composition.

According to another preferred embodiment, said composition further comprises between 30% and 90% by mass in relation to the total mass of the composition of a second cross-linking agent.

According to another preferred embodiment said second cross-linking agent is selected from the group comprising multifunctional poly(ethylene glycol) acrylates (functionality 2-4) comprising in particular SR415, SR610 and Ebecryl 11, and mixtures thereof.

According to another preferred embodiment, said second cross-linking agent is selected from the group comprising difunctional, acrylic, urethane aliphatic resins comprising in particular Ebecryl 4491, Ebecryl 230, Ebecryl 271, Ebecryl 2221 and CN9002.

According to another preferred embodiment, said second cross-linking agent is selected from the group comprising difunctional acrylic, urethane, aromatic resins comprising in particular Ebecryl 210, and mixtures thereof.

According to another preferred embodiment, said second cross-linking agent is selected from the group comprising difunctional epoxy acrylate resins comprising in particular EB3639.

According to another preferred embodiment, said second cross-linking agent is selected from the group comprising acrylic resins comprising in particular Ebecryl 8296, Ebecryl 8232, Ebecryl ODA, Ucecoat 6569, and mixtures thereof.

For the sake of clarity, it is stated that some of the polymerisable monomers according to the invention may act as a cross-linking agent and that in the latter case the preferred concentrations described above are not relevant.

According to a preferred embodiment, said composition further comprises a co-monomer.

According to an even more preferred embodiment said comonomer is selected from the group comprising polybutadiene diacrylates and mono or di-functional monomers, such as tert-butyl acrylate, n-butyl acrylate, lauryl acrylate, lauryl methacrylate, methyl acrylate, stearyl methacrylate, hydroxyethyl acrylate, hydroxyethyl methacrylate, acrylic acid, methacrylic acid, 2-ethoxyethyl methacrylate, 2-ethylhexyl acrylate monomer, 2-ethylhexyl methacrylate, 2-phenyloxyethyl methacrylate, 1-(acryloyloxy)-3-(methacryloyloxy)-2-propanol, di(ethylene glycol) ethyl ether acrylate, ethyl acrylate, ethylene glycol methyl ether acrylate, ethylene glycol phenyl ether acrylate, methyl acrylate, 3-(trimethoxysilyl)propyl methacrylate, methyl methacrylate, poly(ethylene glycol) methyl ether acrylate (Mn of 200 to 10000 g/mol), triethylene glycol dimethacrylate, tert-butyl methacrylate, triethylene glycol monoethylether methacrylate, 3-(tris(trimethylsilyloxy)silyl)propyl methacrylate.

According to a preferred embodiment, said comonomer present in the composition according to the invention has a concentration between 1 and 50% by mass in relation to the total mass of the composition.

According to a preferred embodiment the composition according to the invention comprises a photoinitiator. The person skilled in the art will chose the most suitable photoinitiator as a function of the emission spectrum of the light used.

The photoinitiator may be selected in particular from: biacylphosphine oxide (BAPO), Bis(.eta.5-2,4-cylcopenta-dien-1-yl)-bis(2,6-difluoro-3-(1H-pyrrol-1-yl)-phenyl) titaniuml (Irgacure 784), 1-[4-(2-Hydroxyethoxy)-phenyl]-2-hydroxy-2-methyl-1-propane-1-one (Irgacure 2959), 2,4,6-trimethylbenzoyl-phenylphosphinate oxide (TPO-L), 2,4,6-trimethylbenzoyldiphenylphosphine oxide (TPO), 2,2-dimethoxyphenyl-2-acetophenone (DMPA), camphorquinone or 4,4'-bis(diethylamino)benzophenone, the latter associated with N-phenylglycine (NPG), ethyl-4-(dimethylamino)benzoate (EDB), N-Diisopropylethylamine (DIPEAN) or 4-(Dimethylamino)benzonitrile (DMABN).

Advantageously, the photoinitiator is used in a concentration between 0.2 and 10% by mass.

According to a preferred embodiment, said photoinitiator is TPO-L.

According to another preferred embodiment, the polymerisation is initiated by a chemical activator and more particularly by benzoyl peroxide associated with N-Phenylglycine (NPG), Ethyl-4-(dimethylamino)benzoate (EDB), N-Diisopropylethylamine (DIPEAN) or 4-(dimethylamino)benzonitrile (DMABN).

Advantageously, the chemical activator is used in a concentration between 0.5 and 3% by mass.

According to a preferred embodiment, said composition only comprises said monomer and a photoinitiator or only said monomer, a first or second cross-linking agent and a photoinitiator.

According to an embodiment of the invention, said composition comprises a solvent and even more preferably said solvent is water. According to another preferred embodiment, said solvent is an alcohol and more preferably ethanol or isopropanol.

According to another preferred embodiment, said composition is free of solvent.

According to a preferred embodiment of the invention, said composition comprises a plug.

According to an even more preferred embodiment, said plug is a basic plug and in a quite preferred manner said basic plug is selected from the group comprising KOH, guanidine carbonate, Ca(OH)$_2$, K$_2$CO$_3$, 2-amino-2-methyl-1-propanol (AMP), Na$_2$CO$_3$, resorcinol and NaOH.

The person skilled in the art also has to choose the plug concentrations which are most suitable for this use. According to a much preferred embodiment of the invention, the composition comprises a KOH concentration of between 0 and 8% by mass.

According to a preferred embodiment of the invention, said composition comprises between 0.1 and 5% by mass photoinitiator, between 30 and 90% by mass of a second cross-linking agent, between 1 and 50% by mass polymerisable monomer comprising a phosphate function and a methacrylate function according to the invention and between 1 and 50% by mass co-monomer.

The compositions described in the tables below are preferred more particularly (the quantities are given as a percentage of the total mass of the composition).

TABLE 1

| TPO-L | UDMA | TEGDMA | MDP | tBuA | BM | LMA | LA | KOH, 5M in ethanol |
|---|---|---|---|---|---|---|---|---|
| 1 to 2 | 4.5 to 5.5 | 0 | 55 to 65 | 34.83 | 0.01 to 0.05 | 0 | 0 | 0 |
| 1 to 2 | 0 | 25 to 35 | 20 to 25 | 45.52 | 0.01 to 0.05 | 0 | 0 | 0 |
| 1 to 2 | 0 | 25 to 35 | 10 to 15 | 55.2 | 0.01 to 0.05 | 0 | 0 | 0 |
| 1 to 2 | 4.5 to 5.5 | 0 | 15 to 20 | 74.8 | 0.01 to 0.05 | 0 | 0 | 0 |
| 1 to 2 | 4.5 to 5.5 | 0 | 25 to 30 | 0 | 0.01 to 0.05 | 15 to 25 | 0 | 0 |
| 1 to 2 | 0 | 0 | 40 to 60 | 0 | 0 | 0 | 0 | |
| 1 to 2 | 4.5 to 5.5 | 0 | 25 to 30 | 24.71 | 0.01 to 0.05 | 0 | 5 | 5 to 15 |

TABLE 2

| TPO-L | MEP | tBuA | AA | BM | KOH 5m in ethanol |
|---|---|---|---|---|---|
| 1 to 2 | 10 to 20 | 80 to 90 | 0 | 0.01 to 0.05 | 0 |
| 1 to 2 | 20 to 30 | 70 to 80 | 0 | 0.01 to 0.05 | 0 |
| 1 to 2 | 3 to 7 | 60 to 70 | 15 to 25 | 0.01 to 0.05 | 5 to 15 |
| 1 to 2 | 3 to 7 | 20 to 30 | 25 to 35 | 0.01 to 0.05 | 5 to 15 |
| 1 to 2 | 3 to 7 | 75 to 85 | 5 to 15 | 0.01 to 0.05 | 3 to 7 |

In the context of the present invention, the term "comprises" means that the composition according to the invention includes the cited elements. In a preferred manner, the present invention relates to compositions comprising only the cited elements with the exclusion of any other.

The present invention also relates to a non-invasive method for the adhesion of a material to a biological tissue, for the adhesion of biological tissues to one another, for the adhesion of a glue or a substance to the surface of a biological tissue, surgical sealing for blocking or plugging orifices created by a thread suture or staple or by tissue resection (haemostasis, aerostasis, lymphostasis for example), for blocking an orifice, an incision or a tear in a biological tissue, for stopping bleeding, for covering and protecting a wound, for reinforcing a biological tissue or for fixing and stabiliser a biological tissue, notable in that it comprises the steps:

(i) coating the tissue to be treated with a composition according to the invention
(ii) allowing the composition to penetrate into said tissue,
(iii) inducing the polymerisation of said composition.

In the context of the present invention, the term "biological tissue" denotes preferably non-mineralised biological tissues.

For the sake of clarity, it is specified that in the context of the present invention, the term "biological tissue" does not refer to bones and teeth.

The method according to the invention is advantageously non-invasive. The term "non-invasive" means that the method according to the invention does not include any surgical step consisting of access to the tissue to be treated. Thus, the method according to the invention is performed on a biological tissue that is directly accessible (e.g. the skin) or previously made accessible by other methods.

According to a preferred embodiment, said step (iii) is performed with the aid of UV radiation. The characteristics of the UV radiation used, in particular its power and wavelength, are adapted to the constituents of the composition, in particular to the nature of the polymerisable monomer and its concentration in the composition.

According to another preferred embodiment, said step (iii) is performed by means of visible light radiation.

According to a preferred embodiment, said UV radiation has a wavelength between 350 and 400 nm.

According to a preferred embodiment, said UV radiation has an irradiance power between 20 mW/cm2 and 500 mW/cm2.

The present invention also relates to an assembly of parts comprising a composition according to the invention and a source of UV radiation. Preferably, the source of UV radiation of the assembly of parts can emit UV radiation suitable for polymerising and/or assisting with polymerisation and/or accelerating the polymerisation of the polymerisable monomer of the composition.

According to another embodiment, the present invention also relates to an assembly of parts comprising a composition according to the invention and an initiator of chemical polymerisation.

In the context of the present invention, the term "source of UV radiation" refers to any artificial means capable of producing UV radiation and more particularly radiation with a wavelength between 200 and 400 nm, even more preferably between 300 nm to 400 nm and quite preferably between 350 nm and 400 nm. In a preferred manner said UV radiation is an irradiance power between 20 mW/cm2 and 500 mW/cm2 and even more preferably between 50 mW/cm2 and 150 mW/cm2.

In a more preferred manner, said UV radiation has a wavelength between 350 and 400 nm and power between 50-200 mW/cm2.

DESCRIPTION OF EMBODIMENTS

Materials and Methods
Skin Reaction Test
In Animals

Compositions according to the invention and control compositions were deposited on the backs and abdomens of previously shaved and disinfected rabbits and rats.

The composition is deposited on the surface of the skin and then polymerised using a light irradiation source.

The presence or absence of skin reactions is observed during the application and in the following days.

In Humans

Compositions according to the invention and control compositions were deposited on the front face of the forearm.

The composition is deposited on the surface of the skin and then polymerised by the source of polymerisation.

The presence or absence of skin reactions are observed during the application and in the following days.

In humans and animals, the following compositions were tested:

TABLE 3

| TPO-L (%) | UDMA (%) | TEGDMA (%) | tBuA (%) | MDP (%) | LMA (%) | BM (%) | AA |
|---|---|---|---|---|---|---|---|
| 1.5 | 5 | 0 | 34.8 | 58.7 | 0 | 0.02 | 0 |
| 1.5 | 0 | 29.98 | 45.52 | 23.01 | 0 | 0.02 | 0 |
| 1.5 | 5 | 0 | 34.8 | 0 | 58.7 | 0.02 | 0 |
| 1.5 | 0 | 29.98 | 45.52 | 0 | 23.01 | 0.02 | 0 |
| 1.5 | 4.98 | 0 | 34.83 | | | 0.02 | 5870 |

Peeling Test

Compositions according to the invention and control compositions were deposited on bovine pericardium samples. This step is performed at 20° C. The said pericardium samples were subjected to UV radiation of 395 nm, for a duration of 45 s, in order to trigger the polymerisation of the monomers. The source of radiation was placed 10 cm from the pericardium.

The said pericardium samples were then covered with a 17-thread woven pad, which was then treated with a monomer solution identical to that used in the previous step.

The pericardium samples were subjected to UV radiation under the same conditions as in the previous step.

The resting time of the pad installed between the jaws of the traction machine is one minute, the temperature inside the sample is 30° C. + or −4° C. at the time of starting the test.

Results
Skin Reaction Test

All of the tests carried out on humans and animals with acrylic acid or methacrylic acid based compositions cause skin irritation and/or skin burns.

Rather, the tests carried out with compositions according to the invention comprising MDP and MEP (monomers with an acrylate function and a phosphate function) have shown an absence of apparent skin reactions.

These results clearly indicate that at an equivalent monomer concentration, the compositions according to the invention are less aggressive for the treated tissues.

Peeling Test

Of all the tests carried out, it was observed that the compositions comprising monomers without a phosphate function do not achieve good quality adhesion, i.e. peeling occurs at the interface between the skin and coated fibre web.

Rather, the compositions according to the invention, comprising a phosphate function and an acrylic function make it possible to obtain, regardless of the monomer concentration, good quality adhesion as evidenced by complete peeling in the treated tissue.

It is thus observed that, at an equivalent concentration and with a similar chemical structure, the presence of a phosphate function in the polymerisable monomer used in the composition according to the invention makes it possible to increase the resistance to rupture and ensures the cohesion by penetration into the surface layers of the tissue to be treated (i.e. the strength of the bond).

The invention claimed is:

1. A composition for use as a surgical adhesive for the adhesion of a material to a non-mineralised biological tissue, for the adhesion of non-mineralised biological tissues to one another, for the adhesion of a glue or a substance to the surface of a non-mineralised biological tissue, as surgical sealant, for blocking or plugging orifices created by a thread suture or staple or by a tissue resection, for blocking an orifice, an incision or a tear in a non-mineralised biological tissue, as a haemostatic for stopping bleeding, as a dressing on a non-mineralised biological tissue for covering and protecting a wound, for reinforcing a non-mineralised biological tissue, or for fixing and stabilising a non-mineralised biological tissue, wherein said composition comprises between 10 and 60% by mass relative to the total mass of the composition of a polymerisable monomer comprising a phosphate function or a phosphonate function and a methacrylate function;

wherein the composition comprises a polymerisable monomer of formula I:

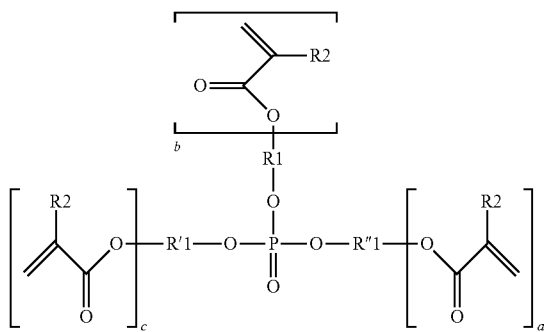

wherein:
R2 is H or CH3;
R1, R1', and R1" are independently of one another a linear polyether radical, a linear or branched aliphatic radical with C1-C50, an aromatic radical of C6-C18, for which the carbon chain of said radicals can be interrupted by O, S, OCONH and/or can comprise one or more alcohol functions;
R1' is H if c=0;
R1" is H if a=0;
b is 1; and
a or c is 1 or 0.

2. The composition according to claim 1, wherein a=0, R2=H or $CH_3$ and R'1 and R1 is a linear aliphatic chain of C1-C12.

3. The composition according to claim 2, wherein a=0, c=0, R2=CH3 and R1 is a linear aliphatic chain of C1-C12.

4. The composition according to claim 1, wherein the polymerisable monomer of formula I is 10-MDP ($C_{14}H_{27}O_6P$) or MEP($C_{12}H_{19}O_8P$).

5. The composition according to claim 1, further comprising between 4% and 30%, by mass in relation to the total mass of the composition, of a first cross-linking agent.

6. The composition according to claim 4, further comprising between 30% and 90%, by mass in relation to the total mass of the composition, of a second cross-linking agent.

7. The composition according to claim 1, further comprising a co-monomer.

8. The composition according to claim 7, wherein said comonomer is selected from the group comprising polybutadiene diacrylates and mono or di-functional monomers such as tert-butyl acrylate, n-butyl acrylate, lauryl acrylate, lauryl methacrylate, methyl acrylate, stearyl methacrylate, hydroxyethyl acrylate, hydroxyethyl methacrylate, acrylic acid, methacrylic acid, 2-ethoxyethyl methacrylate, 2-ethylhexyl acrylate monomer, 2-ethylhexyl methacrylate, 2-phenyloxyethyl methacrylate, 1-(acryloyloxy)-3-(methacryloyloxy)-2-propanol, di(ethylene glycol) ethyl ether acrylate, ethyl acrylate, ethylene glycol methyl ether acrylate, ethylene glycol phenyl ether acrylate, methyl acrylate, 3-(trimethoxysilyl)propyl methacrylate, methyl methacrylate, poly(ethylene glycol) methyl ether acrylate (Mn of 200 to 10000 g/mol), triethylene glycol dimethacrylate, tert-butyl methacrylate, triethylene glycol monoethylether methacrylate, 3-(tris(trimethylsilyloxy)silyl)propyl methacrylate.

9. The composition according to claim 8, wherein said co-monomer has a concentration between 1 and 50% by mass in relation to the total mass of the composition.

10. The composition according to claim 1, further comprising a photoinitiator.

11. The composition according to claim 9, wherein said photoinitiator is selected from the group consisting of bisacylphosphine oxide, Bis(.eta.5-2,4-cylcopentadien-1-yl)-bis(2,6-difluoro-3-(1H-pyrrol-1-yl)-phenyl) titanium, I' 1-[4-(2-Hydroxyethoxy)-phenyl]-2-hydroxy-2-methyl-1-propane-1-one, 2,4,6-trimethylbenzoyl-phenylphosphinate oxide, 2,4,6-trimethylbenzoyldiphenylphosphine oxide, 2,2-dimethoxyphenyl-2-acetophenone, camphorquinone or 4,4'-bis(diethylamino)benzophenone, the latter associated with N-Phenylglycine, Ethyl-4-(dimethylamino)benzoate, N-Diisopropylethylamine and 4-(Dimethylamino)benzonitrile.

12. The composition according to claim 9, wherein said photoinitiator is in a concentration between 0.2 and 10% by mass.

13. The composition according to claim 4, wherein the composition comprises between 0.1 and 5% by mass photoinitiator, between 30 and 90% by mass of a second cross-linking agent, between 10 and 50% by mass of polymerisable monomer comprising a phosphate function and a methacrylate function and between 1 and 50% by mass of co-monomer.

14. A non-invasive method for the adhesion of a material to a non-mineralised biological tissue, for the adhesion of non-mineralised biological tissues to one another, for the adhesion of a glue or a substance to the surface of a non-mineralised biological tissue, surgical sealing, for blocking or plugging orifices created by a thread suture or staple or by a tissue resection, for blocking an orifice, an incision or a tear in a non-mineralised biological tissue, for stopping bleeding, for covering and protecting a wound, for reinforcing a non-mineralised biological tissue or for fixing and stabilising a non-mineralised biological tissue, said non-invasive method comprising the steps:
(i) coating the tissue to be treated with a composition according to claim 1,
(ii) letting the composition penetrate into said tissue,
(iii) inducing the polymerisation of said composition.

* * * * *